United States Patent [19]
Saito et al.

[11] Patent Number: 5,380,319
[45] Date of Patent: Jan. 10, 1995

[54] HEAT USING THERAPEUTIC DEVICE

[75] Inventors: Hidetoshi Saito, Hanno; Makoto Inaba, Tokyo; Motoyuki Tagawa, Tokyo; Toru Nagase, Tokyo, all of Japan

[73] Assignee: Olympus Optical Co., Ltd., Tokyo, Japan

[21] Appl. No.: 955,660

[22] Filed: Oct. 2, 1992

[30] Foreign Application Priority Data

Oct. 7, 1991 [JP] Japan .................. 3-259478

[51] Int. Cl.⁶ .............................................. A61B 17/36
[52] U.S. Cl. ...................... 606/28; 604/96; 604/101
[58] Field of Search ............... 600/4, 10–16; 606/28, 29; 604/96, 101

[56] References Cited

U.S. PATENT DOCUMENTS

| | | | |
|---|---|---|---|
| 4,186,729 | 2/1980 | Harrison | 600/10 |
| 4,423,725 | 1/1984 | Baran et al. | 604/101 |
| 4,662,368 | 5/1987 | Hussein et al. | 606/28 |
| 4,681,122 | 7/1987 | Winters et al. | |
| 5,006,119 | 4/1991 | Ackes et al. | 606/28 |
| 5,019,075 | 5/1991 | Spears et al. | 606/28 |
| 5,114,423 | 5/1992 | Kasprzyk | 606/28 |
| 5,149,319 | 9/1992 | Unger | 600/10 |
| 5,151,100 | 9/1992 | Abele et al. | 602/28 |

FOREIGN PATENT DOCUMENTS 4001086 7/1991 Germany .
63-37669 7/1988 Japan .

*Primary Examiner*—Jerome L. Kruter
*Assistant Examiner*—Rob Clarke
*Attorney, Agent, or Firm*—Frishauf, Holtz, Goodman & Woodward

[57] ABSTRACT

A heat using therapeutic device includes an applicator provided with an insertion section, a balloon enclosing a high frequency warming electrode attached to the insertion section of the applicator; medicine ejecting holes arranged on the balloon; and a medicine passage for connecting the medicine ejecting holes to a medicine mouth piece attached to a rear end of the applicator.

16 Claims, 6 Drawing Sheets

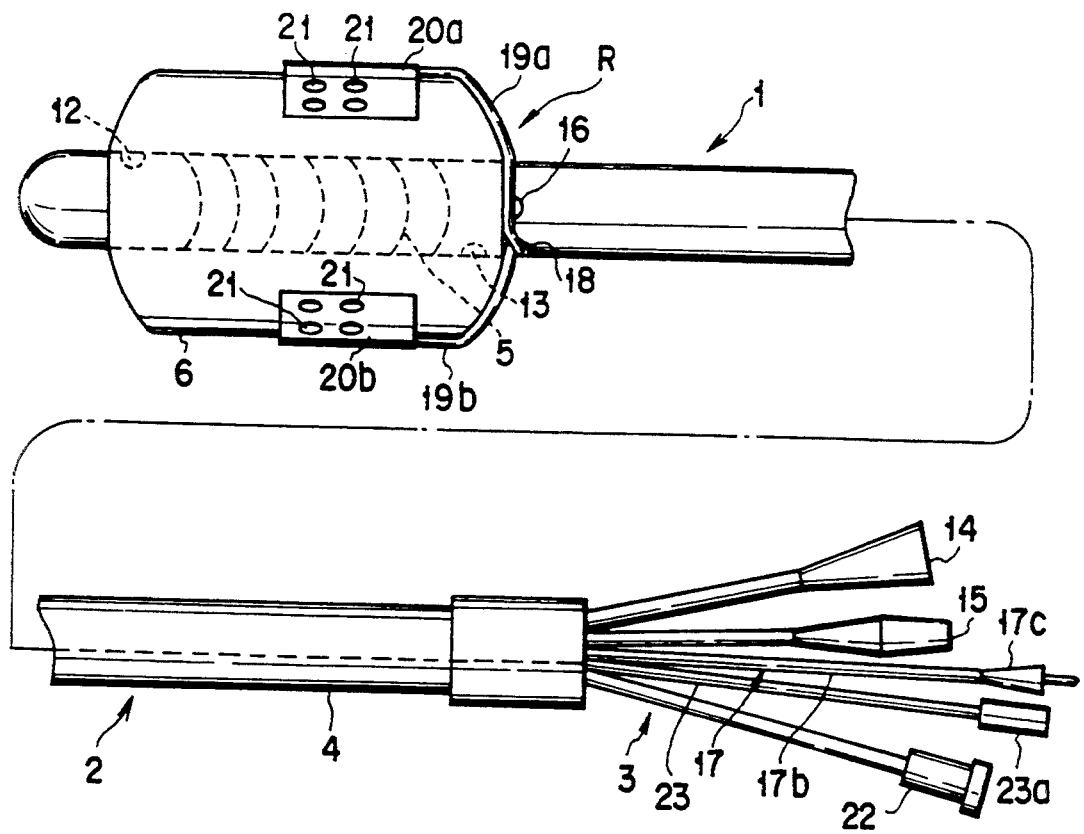
FIG. 1
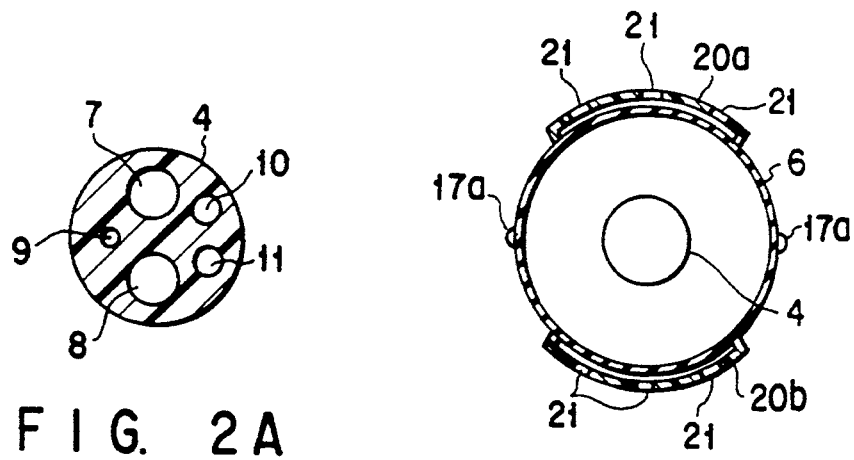
FIG. 2A
FIG. 2B

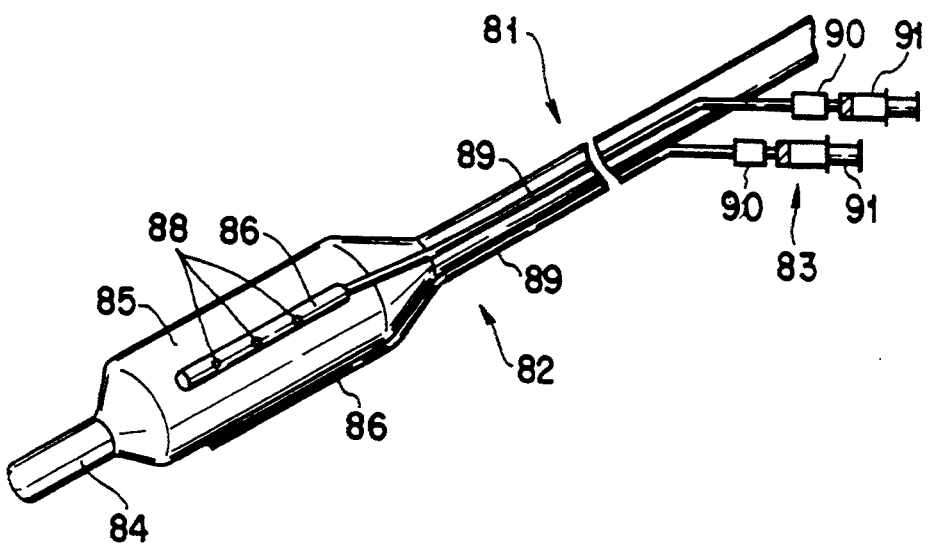
F I G. 13A
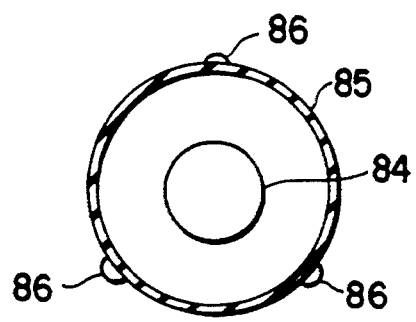
F I G. 13B
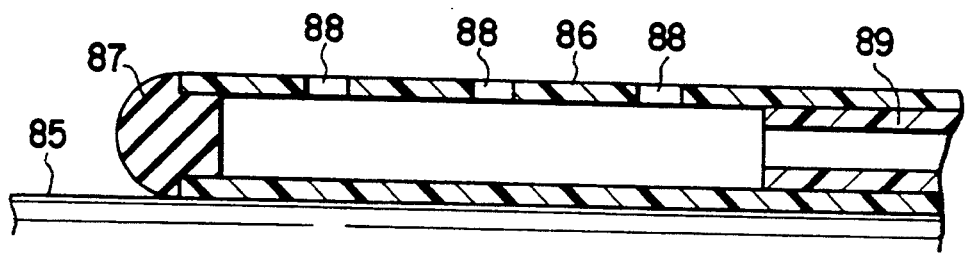
F I G. 13C

HEAT USING THERAPEUTIC DEVICE

BACKGROUND OF THE INVENTION

1. Field of the Invention

The present invention relates to a heat using therapeutic device capable of curing that part in the body cavity of a patient which is affected by cancer, for example, while warming this part to a temperature of about 43° C.

2. Description of the Related Art

As a cancer curing means, attention is now being paid to the method of combining the heat using therapy with anticancer medicine applied. Generally, the anticancer medicine is injected to the patient while applying to him or her the heat using therapy of warming the cancer-affecting part in his body cavity. In order to make the curing or treating effect higher in this case, there has also been employed the method of coating the anticancer medicine directly to the cancer-affecting part and its vicinity in his body cavity.

One of these heat using therapeutic devices in which the heat using therapy is combined with anticancer medicine applied is disclosed in Japanese Patent Publication Sho 63-37669, for example.

According to this heat using therapeutic device, heater and sensors are housed in a inserted section made of flexible material. The anticancer medicine is coated round the inserted section. When the heat using therapeutic device is to be used, the inserted section is inserted to the affected part in the body cavity of the patient and the anticancer medicine round the inserted section is stuck to the cancer-affecting part.

In the case of this conventional device, the anticancer medicine is coated at first round the inserted section and the inserted section thus prepared is then introduced to the affected part in the body cavity of the patient.

The anticancer medicine is kept exposed round the inserted section in this case. When the heat using therapeutic device is to be used, therefore, there is fear that the anticancer medicine round the inserted section is stuck to normal organs in the body cavity of the patient in the course of inserting the inserted section to an object in the body cavity.

This makes it difficult to correctly apply the anticancer medicine to the affected part and to hold it there while applying the heat using therapy to the patient. This is a problem to overcome from the viewpoint of enhancing the curing effect.

SUMMARY OF THE INVENTION

The present invention is intended to eliminate the above-mentioned drawbacks.

The object of the present invention is therefore to provide a heat using therapeutic device capable of more correctly applying anticancer medicine, for example, to the affected part of the patient and more reliably holding it there, while the patient is under the heat using therapy, so as to enhance the curing effect.

This object of the present invention can be achieved by a heat using therapeutic device including an applicator provided with a section inserted into the body cavity of a patient, another section located on the rear end side of the inserted section and outside the patient body, and warming means attached to the inserted section and used when heat using therapy is applied to the patient, said device further comprising balloon means arranged at the inserted section of the applicator to enclose the warming means and provided with a space, into which operating fluid is introduced, formed between the inserted section and the balloon means; means for supplying and exhausting the operating fluid into and out of the space of the balloon means, said means serving to expand the balloon means to fix the applicator in the body cavity of the patient when the operating fluid is supplied to the space; and means having medicine ejecting holes located at one end thereof and in the vicinity of the balloon means and a medicine supply portion located at the other end thereof and outside the patient body, said means serving to connect the medicine supply portion to the medicine ejecting holes to form a medicine passage.

According to the present invention, medicine can be supplied from the medicine supply section located on the rear end side of the applicator to the medicine ejecting holes arranged round the balloon through the medicine passage, while keeping the applicator inserted into the body cavity of the patient and the balloon fixed to the affected part in his body cavity. This can prevent the medicine from being stuck to normal organs in his body cavity even in the course of inserting the applicator to an object in his body cavity. Therefore, the medicine can be correctly applied to the affected part and the curing effect can be enhanced to a greater extent by a combination of the medicine and the heat using therapy applied.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 1 schematically shows the heat using therapeutic device according to a first embodiment of the present invention;

FIG. 2A is a sectional view showing a shaft at the inserted section of the device;

FIG. 2B is a sectional view showing a balloon;

FIG. 13A is a perspective view showing the whole of the heat using therapeutic device according to seventh embodiment of the present invention;

FIG. 13B is a sectional view showing a balloon; and

FIG. 13C is a perspective view showing a main portion of the front end of the medicine injecting tube.

DETAILED DESCRIPTION OF THE PREFERRED EMBODIMENTS

Figure 3:
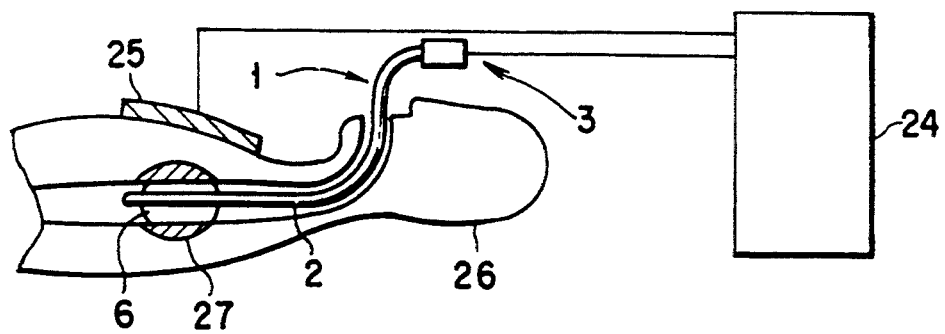
FIG. 3 schematically shows the heat using therapeutic device according to the first embodiment of the present invention used.

A first embodiment of the present invention will be described referring to FIGS. 1 through 3. FIG. 1 schematically shows the heat using therapeutic device according to the first embodiment of the present invention and reference numeral 1 represents an applicator used for heat using therapy. The applicator 1 includes a section 2 inserted into the body cavity of the patient and a section 3 connected to the rear end of the inserted section 2.

The inserted section 2 includes a shaft 4 which is a multi-hole tube. A warming electrode 5 of high frequency is arranged at the front end portion of the shaft 4. An expansible balloon 6 made of soft material is arranged around the high frequency warming electrode 5.

The shaft 4 includes therein water supply, drain, cable, sensor and medicine holes 7, 8, 9, 10 and 11. Front ends of the water supply and drain holes 7 and 8 in the shaft 4 are communicated with a space in the balloon 6 through their openings 12 and 13. Their rear ends are communicated with water supply and drain tubes 14 and 15, respectively.

The front end of the sensor hole 10 terminates with an opening 16 which is formed in the shaft 4 at the rear end of the balloon 6. A temperature sensor 17 is inserted into the sensor hole 10 through the rear end of the shaft 4.

The temperature sensor 17 is a thermocouple, for example. In the case of this temperature sensor 17, a set of temperature detectors 17a arranged at the front end of the shaft 4 are connected to a contact 17c, which is arranged on the rear side of the shaft 4, via lead line 17b. The temperature detectors 17a of the temperature sensor 17 are pulled outside through the opening 16 at the front end portion of the shaft 4 and bonded on the balloon 6, opposing to each other at an angle of 180°, as shown in FIG. 2B.

The medicine hole 11 is communicated with a branching opening 18 formed in the shaft 4 at the rear side of the balloon 6. Rear ends of paired medicine tubes 19a and 19b are connected to the branching opening 1a. These medicine tubes 19a and 19b extend from the branching opening 18 onto the balloon 6.

A pair of sheet-like medicine ejecting covers 20a and 20b are arranged on the balloon 6, opposing to each other at an angle of about 180°. Each of the medicine ejecting covers 20a and 20b has plural medicine ejecting holes 21.

The rim portion of each of the medicine ejecting covers 20a and 20b is bonded and fixed to the balloon 6. Front ends of the medicine tubes 19a and 19b are bonded and fixed in spaces of their corresponding medicine ejecting covers 20a and 20b, communicating with the spaces. The medicine hole 11 is connected to a medicine mouth piece 22 on the rear end side of the shaft 4 and the medicine mouth piece 22 can be connected to a syringe (not shown). The medicine ejecting holes 21, spaces between the medicine ejecting covers 20a, 20b and the balloon 6, medicine tubes 19a and 19b, the medicine hole 11 and the medicine mouth piece 22 are communicated with one another to form a medicine passage R.

The front end of the cable hole 9 is communicated with an opening arranged in the balloon 6. A high frequency current cable 23 is held in the cable hole 9. The front end portion of the cable 23 is extended outside the shaft through the opening of the cable hole 9. The extended front end portion of the cable 23 is wound round the shaft 4 to form the high frequency warming electrode 5. The rear end of the cable 23 is connected to a high frequency connector 23a on the rear end side of the shaft 4.

The connected section 3 of the applicator 1 is connected, as shown in FIG. 3, to a body 24 of the heat using therapeutic device in which a high frequency power source is housed. An external electrode 23 is connected to the heat using therapeutic device body 24. The electrode area of the external electrode 25 is made larger than that of the high frequency warming electrode 5 on the front end portion of the applicator 1. When the heat using therapeutic device body 24 is under operation, high frequency current is allowed to flow between the high frequency warming electrode 5 on the applicator 1 and the external electrode 25.

It will be described how the heat using therapeutic device arranged as described above is operated. When the heat using therapy is to be applied to a patient using the device body 24, the inserted section 3 of the applicator 1 is inserted into the body cavity of the patient. The balloon 6 of the applicator 1 is positioned at an affected part in the body 26 of the patient and expanded and fixed there.

The external electrode 25 is positioned on the body 26 of the patient to oppose to the high frequency warming electrode 5 of the applicator 1 in the body 26 of the patient and fixed there. When the applicator I and the external electrode 25 are set like this, a syringe (not shown) in which medicine for cancer, for example, is contained is connected to the medicine mouth piece 22. The medicine is then ejected into the medicine hole 11 in the shaft a through the medicine mouth piece 22 while pushing the piston into the syringe.

The medicine thus ejected is pressure-fed into the front end of the shaft 4 through the medicine hole 11 and into the spaces between the medicine ejecting covers 20a, 20b and the balloon 6 through the medicine tubes 19a and 19b and spread or sprayed on the affected part 27 through the medicine ejecting holes 21 of the medicine ejecting covers 20a and 20b.

The heat using therapeutic device body 24 is driven under this state to apply high frequency current between the high frequency warming electrode 5 of the applicator 1 and the external electrode 25. Current thus applied is concentrated in this case on the high frequency warming electrode 5 of the applicator 1 whose surface area is smaller than that of the external electrode 25. The effected part 27 in the body of the patient and around the high frequency warming electrode can be thus warmed to help the anti-cancer medicine applied cure cancer.

According the heat using therapeutic device. the applicator 1 is inserted into the body cavity of the patient and the balloon 6 is fixed corresponding to the affected part in the patient body. Medicine is then supplied from the rear end of the applicator 1 into the medicine passage R and spread or sprayed outside through the medicine ejecting holes 21 of the medicine ejecting covers 20a and 20b. Therefore, the anticancer medicine can be more correctly applied to the affected part 27 in the patient body.

When the applicator 1 passed through the body cavity of the patient in the course of inserting it to an object, some of medicine was conventionally stuck to normal organs in the body cavity, but this can be overcome by the above-described heat using therapeutic device. Therefore, the anticancer medicine can be stuck to the effected part 27 and held there with more reliability while applying the heat using therapy to the affected part 27. The curing effect of the affected part 27 can be thus increased by a combination of the medicine and the heat using therapy applied.

When the heat using therapy is being applied to the affected part 27 in the body cavity of the patient, the anticancer medicine can be spray to the affected part 27 without pulling applicator 1 out of the body cavity of the patient. This enables the spraying of medicine to be made simpler and the operating of the device to be made easier, thereby reducing the burden of the operator.

When inflammable gas is present around the affected part 27 in the body cavity of the patient, it can be sucked outside the patient body through the medicine ejecting holes 21. This enables the heat using therapy to be applied to the affected part 27 with higher safety.

Figure 4:
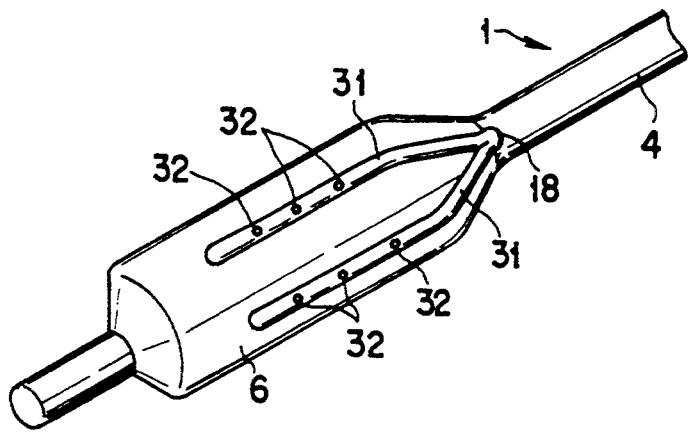
FIG. 4 is a perspective view showing a main portion of the heat using therapeutic device according to a second embodiment of the present invention.
Figure 5:
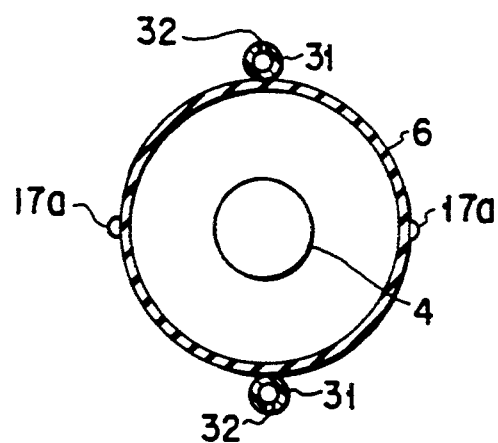
FIG. 5 is a sectional view showing another balloon for the second heat using therapeutic device.

FIGS. 4 and 5 show the heat using therapeutic device according to a second embodiment of the present invention. Both rear ends of paired spraying tubes (or medicine paths) 31 are connected to the branching opening 18 of the shaft 4 of the first embodiment while both front end portions thereof are bonded and fixed on the balloon 6, and medicine spraying holes 32 are formed in the wall of each of the spraying tubes 31. The paired spraying tubes 31 are fixed on the balloon 6. locating substantially central between the paired temperature detectors 17a and 17a of the temperature sensor 17, as shown an FIG. 5.

According to the second heat using therapeutic device, the applicator 1 is inserted into the body cavity of the patient and the balloon is fixed, corresponding to the affected part 27 in the patient body. Medicine is then supplied into the medicine holes 11 through the medicine mouth piece 22 located on the rear end side of the applicator 1, further into the spray tubes 31 and sprayed to the affected part 27 through the medicine ejecting holes 32 of the tubes 31. Therefore, the anticancer medicine can be more correctly stuck to the affected part 27 in the body cavity of the patient as seen in the case of the first device, thereby enabling same effect as in the case of the first device to be achieved.

Each of the spraying tubes 31 which is provided with medicine ejecting holes 32 is fine. This can prevent the diameter of the balloon 6 from becoming large, thereby reducing pain the patient feels when the applicator 1 is inserted into the body cavity of the patient.

Each of the spraying tubes 31 on the balloon 6 is positioned remote enough from both of the temperature detectors 17a of the temperature sensor 17. When the anticancer medicine is ejected into the body cavity of the patient through the medicine ejecting holes 32 of the tubes 31 while applying the heat using therapy to the patient, therefore, temperature at the area adjacent to each of the temperature detectors 17a of the temperature sensor 17 cannot be rapidly changed, thereby enabling more reliable cure to be kept.

Even when three or more temperature detectors 17a of the temperature sensor 17 are used, each of the spraying tubes 31 on the balloon 6 is fixed central between its two adjacent detectors 17a. This enables same effect as above to be achieved.

Figure 6:
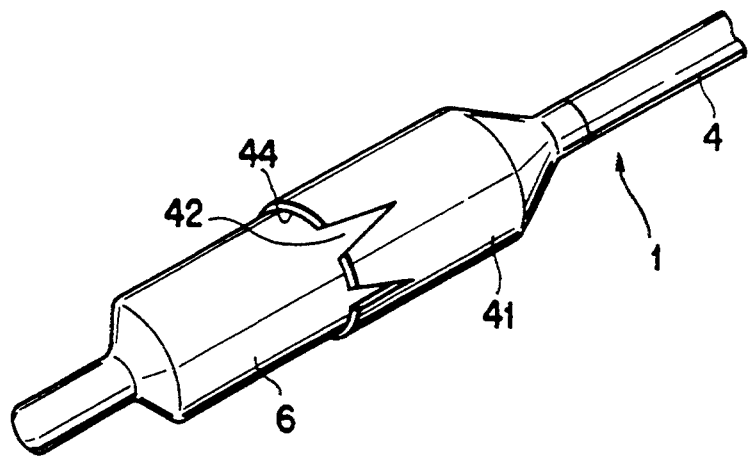
FIG. 6 is a perspective view showing a main portion of the heat using therapeutic device according to a third embodiment of the present invention.
Figure 7:
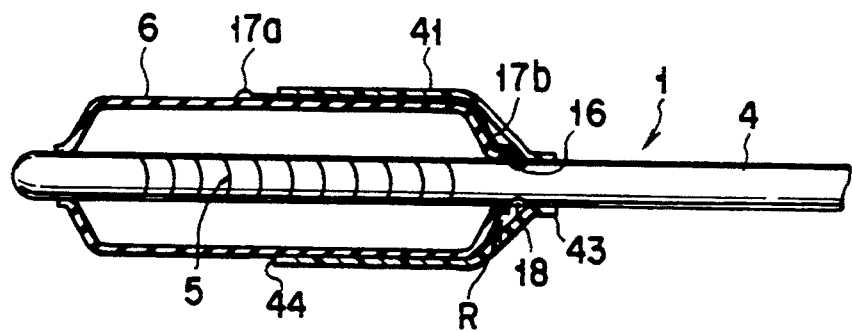
FIG. 7 is a sectional view showing the main portion of the third heat using therapeutic device.

FIGS. 6 and 7 show the heat using therapeutic device according to a third embodiment of the present invention. An outer cylindrical cover 41 is arranged round the balloon 6. covering substantially the half of the balloon 6. As shown in FIG. 7, the outer cover 41 has large and small diameter portions and its large diameter portion has a diameter substantially same as the outer diameter of the balloon 6 while its small diameter portion has a diameter substantially same as the outer diameter of the shaft 4. Further, the large diameter portion of the outer cover 41 is provided with spraying grooves 42 each of which is formed by cutting away the front end of the large diameter portion in the axial direction of the outer cover 41.

In the case of the outer cover 41, its small diameter portion is fixed to the shaft 4 on the rear and side of the balloon 6 while keeping the front end of its large diameter portion positioned substantially at the center of the balloon 6 when viewed in the axial direction of the balloon 6.

The front end of the small diameter portion or fixed portion 43 of the outer cover al round the shaft 4 is positioned rearer, as shown in FIG. 7, than the openings 16 and 1a communicated with the sensor and medicine holes 10 and 11, respectively. Each of the temperature detectors 17a of the temperature sensor 17 pulled out of the sensor hole 10 through the opening 16 extends from the front end of the outer cover 41 onto the balloon 6, passing between the balloon 6 and the outer cover 41, and fixed there while being exposed outside the outer cover 41.

The front end rim 44 of the large diameter portion of the outer cover 41 is bonded and fixed on the balloon 6 while leaving the spraying grooves 42 neither bonded nor fixed. These spraying grooves 42 therefore form the medicine ejecting holes. The spraying grooves. the space between the balloon 6 and the outer cover 41 and the medicine hole 11 cooperate to from the medicine passage R.

According to the third heat using therapeutic device, the applicator 1 is inserted into the body cavity of the patient and the balloon 6 is fixed, corresponding to the affected part 27 in the body cavity of the patient. Medicine is supplied, under this state, into the medicine hole 11 through the medicine mouth piece 22 located on the rear end side of the applicator 1, then into the space between the balloon 6 and the outer cover 41 through the branching opening 1a, and sprayed to the affected part 27 in the body cavity of the patient through the spraying grooves 42 of the outer cover 41. Therefore, the anticancer medicine, for example, can be stuck to the affected part 27 with more reliability, thereby enabling same effect as in the case of the first embodiment to be achieved.

Further, the anticancer medicine is sprayed to the affected part 27 and its vicinity along the spraying grooves 42. Therefore, it can be equally sprayed to the whole of the affected part 27, thereby enabling the curing effect of the affected part 27 to be increased to a greater extent.

Figure 8:
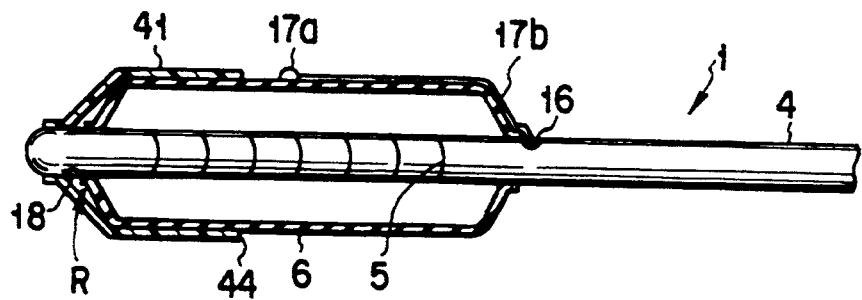
FIG. 8 is a sectional view showing a variation of the main portion of the third heat using therapeutic device.

The shape of each of the spraying grooves 42 is not limited to the one shown in FIG. 6 but it may be variously changed. Further, the outer cover 41 may be arranged at the front end side of the balloon 6, as shown in FIG. 8.

Figure 9:
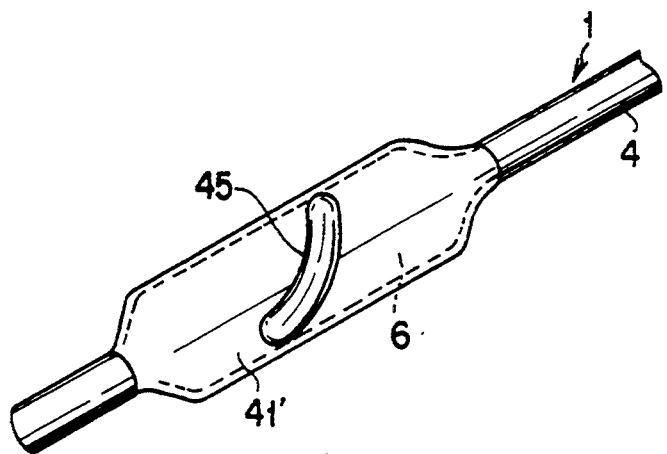
FIG. 9 is a perspective view showing a main portion of the heat using therapeutic device according to a fourth embodiment of the present invention.

As seen in the case of a fourth heat using therapeutic device shown in FIG. 9. it may be arranged that an outer cover 41' covers the whole of the balloon 6 and that an arc-like spraying groove is formed round the outer cover 41'.

Figure 10:
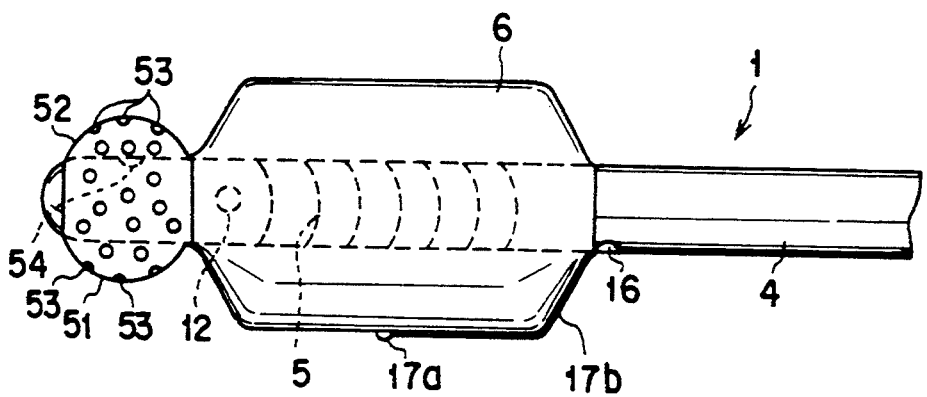
FIG. 10 is a sectional view showing a main portion of the heat using therapeutic device according to a fifth embodiment of the present invention.

FIG. 10 shows the heat using therapeutic device according to a fifth embodiment of the present invention. Another balloon 51 provided with holes is attached to the shaft 4 on the front end side of the balloon 6. A body 52 of this balloon 51 is provided with plural medicine ejecting holes 53, which are uniformly arranged over the entire surface of the balloon 51. That portion of the shaft 4 which is in the holes-provided balloon 51 has an opening 54 communicated with the medicine hole 11.

When the heat using therapy is to be applied to the body 26 of the patient, the applicator 1 is inserted into the body cavity and when the holes-provided balloon 51 reaches the affected part 27, a syringe in which the anticancer medicine. for example, is contained is connected to the medicine mouth piece 22. The piston of the syringe is pushed into the syringe and the anticancer medicine in the syringe is thus supplied from the medicine mouth piece 22 into the holes-provided balloon 51, passing through the medicine hole 11 and the opening 54. The anticancer medicine is then ejected and sprayed to the affected part 27 through the medicine ejecting holes 53.

While keeping the anticancer medicine stuck to the affected part 27, the applicator 1 is a little pushed from this medicine-sprayed position into the cavity of the body to position the balloon 6 at the affected part 27. The heat using therapeutic device is driven under this state through its main unit 24 to cause high frequency current to flow between the high frequency warming electrode 5 of the applicator 1 and the external electrode 25. The affected part 27 in the body cavity of the patient is thus warmed to enhance the effect of the therapy applied.

According to the fifth device, the applicator 1 is inserted into the body cavity of the patient and the holes-provided balloon 51 is fixed, corresponding to the affected part 27. Medicine is then supplied into the holes-provided balloon 51, passing through the medicine mouth piece 22, the medicine hole 11 and the medicine ejecting opening 54. and sprayed to the affected part 27 through the medicine ejecting holes 53. The anticancer medicine, for example, can be therefore stuck to the affected part 27 with more reliability, thereby enabling same effect as in the case of the first embodiment to be attained.

Figure 11:
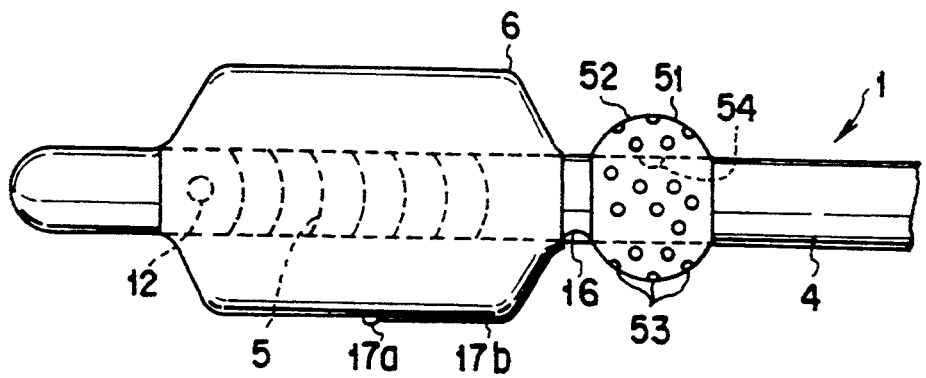
FIG. 11 is a sectional view showing a variation of the main portion of the fifth heat using therapeutic device.

Further, the medicine ejecting holes 53 of the holes-provided balloon 51 are arranged all along the circumference of the balloon body 52. Therefore, the anticancer medicine can be sprayed to the affected part 27 with more reliability. The holes-provided balloon 51 may be located on the rear end side of the balloon 6, as shown in FIG. 11. Same effects as in the case of the fifth device can be attained in this case.

FIGS. 12A through 12D Show the heat using therapeutic device according to a sixth embodiment of the present invention. Reference numeral 61 denotes an applicator for the heat using therapy. The applicator 61 includes a section 62 inserted into the body cavity of the patient and a section 63 connected to the rear end of the inserted section 62.

Figure 12A:
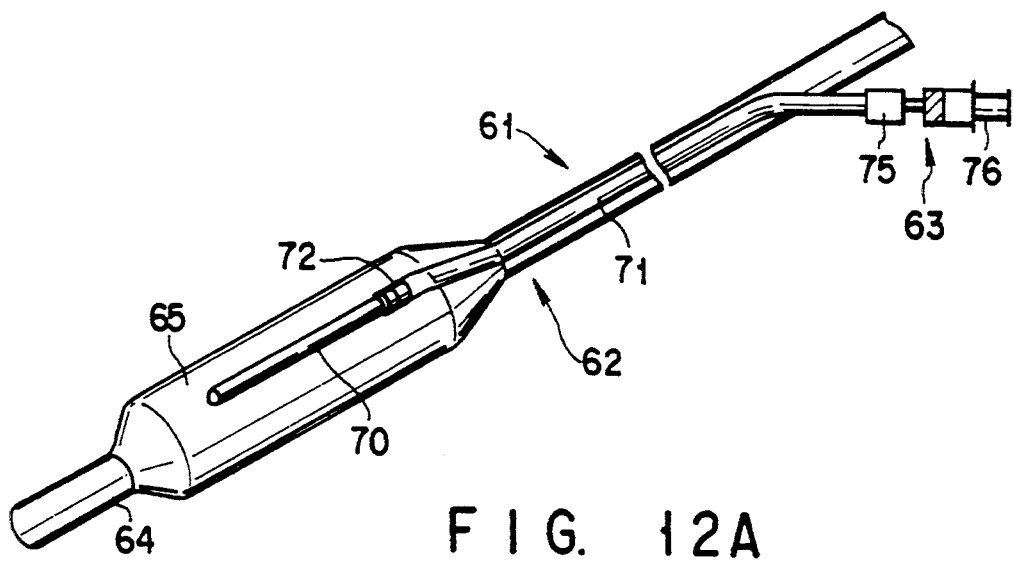
FIG. 12A is a perspective view schematically showing the whole of the heat using therapeutic device according to a sixth embodiment of the present invention.
Figure 12B:
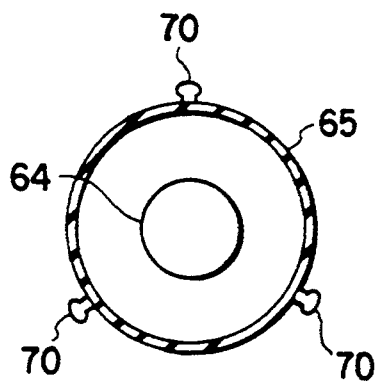
FIG. 12B is a sectional view showing a balloon.
Figure 12C:
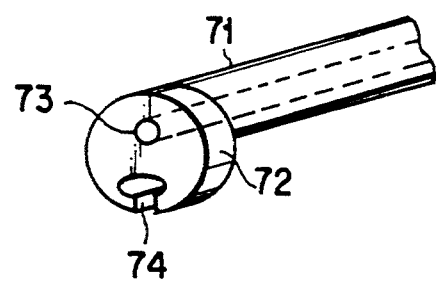
FIG. 12C is a perspective view showing a main portion of the front end of the medicine injecting tube.
Figure 12D:
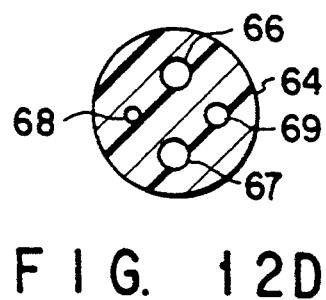
FIG. 12D is a sectional view showing a shaft.

The inserted section 62 includes a shaft 64 provided with four tubes therein, as shown in FIG. 12D. Same high frequency warming electrode 5 as the one in the case of the first device is arranged at the front end portion of the shaft 64. Further, an expansible balloon 65 is provided around the high frequency warming electrode 5.

The shaft 64 includes therein water supply, drain, cable and sensor holes 66, 67, 68 and 69. These water supply, drain, cable and sensor holes are same in structure as those in the case of the first device.

Plural guide rails 70 are projected, extending on the balloon 65 in the axial direction thereof, as shown in FIG. 12B. Further, a medicine injecting tube 71 is arranged on the shaft 64.

A slider 72 made of X-ray impermeable material and freely slidable along the guide rail 70 on the balloon 65 is fixed to the front end of the medicine ejecting tube 71, as shown in FIG. 12C. The slider 72 is provided with a medicine ejecting opening 73, which is communicated with the medicine injecting tube 71, and also with a guide groove 74, which is freely slidably fitted onto its corresponding guide rail 70 on the balloon 65.

A medicine mouth piece 75 is attached to the rear end of the medicine injection tube 71 and a syringe 76 in which anticancer medicine, for example, is contained is detachably connected to the medicine mouth piece 75.

When the heat using therapy is to be applied to the affected part 27 in the body cavity of the patient, the applicator 61 is inserted into the body cavity as seen in the case of the first device. Positions of the affected part 27 and the slider 72 can be confirmed this time by X-ray.

When it is confirmed that the slider 72 has reached the affected part 27, the piston of the syringe 76 is pushed into the syringe 76 to supply the anticancer medicine into the medicine injecting tube 71 and the anticancer medicine is then ejected and sprayed to the affected part 27 through the medicine ejecting opening 73 of the slider 72.

When the medicine is sprayed in this manner, the slider 72 can be moved in the axial direction of the applicator 61 by moving the medicine mouth piece 75 forward and backward by hand. The anticancer medicine, for example, can be thus sprayed all over the affected part 27.

While keeping the anticancer medicine stuck to the affected part 27, high frequency current is caused to flow between the high frequency warming electrode 5 of the applicator 61 and the external electrode 25 to cure the affected part 27.

According to the sixth device, same effects as in the case of the first device can be attained. In addition, the anticancer medicine can be sprayed all over the affected part 27 with more reliability. The curing effect can be thus enhanced to a still greater extent.

FIGS. 13A through 13C show the heat using therapeutic device according to a seventh embodiment of the present invention. Reference numeral 81 denotes an applicator for the heat using therapy. It includes a section 82 inserted into the body cavity of the patient and a section 83 connected to the rear end of the inserted section 82.

The inserted section 82 includes a shaft 84 which is same in structure as the one 64 of the sixth device. The high frequency warming electrode 5 same as the one of the first device is arranged round the front end portion of the shaft 84. An expansible balloon 85 is arranged around the high frequency warming electrode 5.

Three spraying tubes 86 are fixed on the balloon 85. extending in the axial direction of the balloon, as shown in FIG. 13B. The open front end of each of the spraying tubes 86 is closed by a rubber cap 87, as shown in FIG. 13C.

Medicine ejecting holes 8a are formed in the wall of each of the spraying tubes 86 along the axial direction thereof. A medicine mouth piece 90 is attached to the rear end of each of the medicine injecting tubes 89 and a syringe 91 in which anticancer medicine, for example, is contained is detachably connected to each of the medicine mouth piece 90.

Three spraying tubes 86 are connected to their corresponding medicine injecting tubes 89, which are different from one another in length to show what positions they have on the balloon 85.

When the heat using therapy is to be applied to the affected part in the body cavity of the patient, the applicator 81 is inserted into the body cavity and the balloon 85 is fixed, corresponding to the affected part 27. as seen in the case of the first device. The operator then selects one of the medicine injecting tubes 89 whose spraying tube 86 is directed in a direction in which he wishes to spray the anticancer medicine. The syringe 91 is connected to the medicine mouth piece 90 of this selected medicine injecting tube 89. The anticancer medicine is thus supplied into the medicine injecting tube 89 through the medicine mouth piece 90 and ejected and sprayed to the affected part 27 through the medicine ejecting holes 88 of the spraying tube 86.

While keeping the anticancer medicine stuck to the affected part 27, high frequency current is then caused to flow between the high frequency warming electrode 5 of the applicator 8a and the external electrode 25 to cure the affected part 27.

According to the seventh embodiment, same effects as those achieved by the first device can be attained. In addition, the operator can concentrate the anticancer medicine in whatever directions he wants and the curing effect can be thus enhanced to a greater extent.

Further, those medicine spraying directions which cannot be viewed by eyes of the operator can be confirmed by the medicine injecting tubes 89 which are different from one another in length, thereby enabling the device to be more easily handled. This may be confirmed by colors and indexes different every mouth piece 90 connected to medicine injecting tube 89.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

What is claimed is:

1. A heat using therapeutic device including an applicator provided with a first section that is insertable into a body cavity of a patient, a second section located on a rear end side of the first section and adapted to be positioned outside a body of the patient, and warming means attached to the first section for use when a heat therapy is to be applied to the patient, said heat using therapeutic device further comprising:

balloon means which is formed of a flexible material, said balloon means being arranged at the first section of the applicator to enclose the warming means, and said balloon means forming a space into which an operating fluid is introduced;

means for supplying and exhausting the operating fluid into and out of the space formed by the balloon means, said means for supplying and exhausting the operating fluid, expanding the balloon means to fix the applicator in the body cavity of the patient by supplying the operating fluid to the space formed by the balloon means; and medicine releasing means having a first section side and a second section side for releasing a medicine from a region near the warming mean, said medicine releasing means having a medicine ejecting portion formed on either an inner or outer surface portion of the balloon means without penetrating through the balloon means, a medicine supply portion formed on the second section side of the medicine releasing means, and a medicine passage for enabling a communication between the medicine ejecting portion and the medicine supply portion.

2. The heat using therapeutic device according to claim 1, wherein:

the medicine releasing means includes a shaft provided in the first section of the applicator, the shaft being provided with a plurality of lumens therein; and the warming means includes a high frequency warming electrode attached to a front end portion of the shaft.

3. The heat using therapeutic device according to claim 2, wherein the shaft includes:

a medicine hole for passing a medicine therethrough;

a fluid hole, through which the operating fluid is supplied into and exhausted out of the balloon means;

a cable hole for a high frequency current cable that is connectable to the high frequency warming electrode; and a sensor hole for a plurality of lead lines for a plurality of temperature sensors that are bonded and fixed on the balloon means.

4. The heat using therapeutic device according to claim 2, wherein the shaft includes:

a medicine hole for passing a medicine therethrough;

a fluid hole through which the operating fluid is supplied into and exhausted out of the balloon means; and a medicine passage forming means that includes connecting means for connecting the medicine hole with at least one medicine ejecting hole of the therapeutic device.

5. The heat using therapeutic device according to claim 4, wherein:

said connecting means includes sheet-like medicine ejecting covers which together with said balloon means form another space, said medicine ejecting covers being respectively bonded on the balloon means at a rim portion of said medicine ejecting covers, said medicine ejecting covers having medicine ejecting holes formed therein in an area which is not bonded on the balloon means; and said connecting means further including medicine tubes that are connected to a rear end portion of the medicine hole, a front end portion of said medicine tubes being connected to said another space provided between the medicine ejecting covers and the balloon means.

6. The heat using therapeutic device according to claim 4, wherein:

a rear end portion of said connecting means is connected to a front end portion of the medicine hole, and a front end portion of said connecting means has a plurality of medicine tubes provided therein, each medicine tube being fixed on the balloon means; and each of the medicine tubes has a plurality of medicine ejecting holes formed therein.

7. The heat using therapeutic device according to claim 4, wherein said connecting means includes:

an outer cover having first and second end portions, the outer cover covering substantially one half of the balloon means; and a first section of the outer cover being fixed on the shaft at the first end portion of the outer cover; and a second section of the outer cover at the second end portion of the outer cover extending to a center of the balloon means when viewed in an axial direction of the balloon means; and the first section of the outer cover having an opening therein which is connected to the medicine hole in the shaft, and the second section of the outer cover, having a plurality of medicine ejecting holes.

8. The heat using therapeutic device according to claim 4, wherein:

said connecting means includes an outer cover covering all of the balloon means; and a plurality of medicine ejecting holes are formed in the outer cover along an outer circumference of the outer cover.

9. The heat using therapeutic device according to claim 4, wherein said connecting means includes:

a further balloon means positioned adjacent to the first-mentioned balloon means on the shaft;

said further balloon means having a plurality of medicine ejecting holes formed therein.

10. The heat using therapeutic device according to claim 1, wherein:

the medicine ejecting portion is formed on an outer surface of the balloon means.

11. The heat using therapeutic device according to claim 1 wherein the space formed by the balloon means surrounds at least a portion of said first section.

12. The heat using therapeutic device according to claim 2, wherein said shaft includes:

a hole through which the operating fluid is supplied into and exhausted out of the balloon means;

guide rails projected on the balloon means, said guide rails extending in an axial direction of the balloon means; and a medicine passage forming means for forming the medicine passage, said medicine passage forming means including:

a medicine injecting tube arranged on the shaft;

a slider fixed to a front end of the medicine injecting tube, said slider being freely slidable along the guide rails on the balloon means; and a medicine ejecting opening that communicates with the medicine injecting tube.

13. The heat using therapeutic device according to claim 12, wherein said slider comprises an X-ray impermeable material.

14. The heat using therapeutic device according to claim 2, wherein:

said shaft includes a hole through which the operating fluid is supplied into and discharged out of the balloon means, and said therapeutic device further comprising:

a medicine passage forming means for forming the medicine passage, said medicine passage forming means including:

a plurality of spraying tubes that respectively extend on the balloon means in an axial direction of the balloon means;

each spraying tube having a closed front end portion and being provided with a plurality of medicine ejecting holes in a wall portion thereof; and a plurality of medicine injecting tubes arranged on the shaft, each medicine injecting tube having a front end portion thereof connected to a rear end portion of a respective one of the plurality of spraying tubes.

15. The heat using therapeutic device according to claim 14, wherein:

said plurality of spraying tubes are arranged side-by-side on the balloon means in a circumferential direction of the balloon means;

each of said plurality of medicine injecting tubes is respectively connected to a respective one of the spraying tubes; and the plurality of medicine injecting tubes differ from each other in a respective length dimension thereof to facilitate an identification of respective ones of the spraying tubes to which each of the plurality of injecting tubes is connected.

16. The heat using therapeutic device according to claim 10, wherein:

the medicine ejecting portion comprises first and second spaced-apart medicine ejecting portions respective positioned on the outer surface of the balloon means.

* * * * *